United States Patent [19]

Kunz et al.

[11] 4,141,968

[45] Feb. 27, 1979

[54] NOVEL SALTS OF 1,3-BIS-(β-ETHYLHEXYL)-5-AMINO-5-METHYL-HEXAHYDROPYRIMIDINE IN COMPOSITIONS HAVING BACTERIOSTATIC ACTIVITY

[75] Inventors: Wilhelm Kunz; Klaus Posselt, both of Wachtberg-Villiprott; Manfred Löhner, Bonn-Bad Godesberg, all of Fed. Rep. of Germany

[73] Assignee: Doll GmbH, Bonn-Bad Godesberg, Fed. Rep. of Germany

[21] Appl. No.: 738,510

[22] Filed: Nov. 3, 1976

[30] Foreign Application Priority Data

Jun. 16, 1976 [DE] Fed. Rep. of Germany ....... 2626935

[51] Int. Cl.² ...................... A61K 9/68; C07D 239/04
[52] U.S. Cl. ......................... 424/48; 424/54; 424/55; 424/251; 544/322
[58] Field of Search ................. 260/256.4 H, 256.4 B; 424/48, 54, 55

[56] References Cited

U.S. PATENT DOCUMENTS

| | | | |
|---|---|---|---|
| 2,837,463 | 6/1958 | Fosdick et al. | 424/48 |
| 2,907,768 | 10/1959 | Lewenstein | 260/285 |
| 3,072,529 | 1/1963 | Sanders et al. | 424/251 |
| 3,671,626 | 6/1972 | Felger | 424/49 |
| 3,887,701 | 6/1975 | Nachtigal | 424/55 |
| 3,934,002 | 1/1976 | Haefele | 424/54 |
| 3,937,805 | 2/1976 | Harrison | 424/54 |
| 3,946,013 | 3/1976 | Tauscher et al. | 424/251 |
| 4,010,160 | 3/1977 | Lange et al. | 260/256.4 H |

FOREIGN PATENT DOCUMENTS

| | | |
|---|---|---|
| 2411383 | 9/1974 | Fed. Rep. of Germany. |
| 2125207 | 9/1972 | France ............................. 260/256.4 H |

OTHER PUBLICATIONS

F. A. Barkley et al., *Antimicrobial Agents Annual* 1960, conference in Wash. D. C., 10/26-28/1960, pp. 507-519, Plenum Press, N.Y., 1961.

T. Higuchi et al., J. Pharm. Sci., 53, 6 (Jun. 1964), pp. 644-651.

*Primary Examiner*—Lewis Gotts
*Assistant Examiner*—Molly C. Eakin
*Attorney, Agent, or Firm*—Sprung, Felfe, Horn, Lynch & Kramer

[57] ABSTRACT

Novel salts of 1,3-bis-(β-ethylhexyl)-5-amino-5-methyl-hexahydropyrimidine (hexetidine) with substituted benzoic acids and processes of preparing these salts are described. These novel salts have useful bacteriostatic activity and show stability in storage. The invention accordingly comprises compositions containing the novel salts and having bacteriostatic activity.

12 Claims, No Drawings

NOVEL SALTS OF 1,3-BIS-(β-ETHYLHEXYL)-5-AMINO-5-METHYL-HEXAHYDROPYRIMIDINE IN COMPOSITIONS HAVING BACTERIOSTATIC ACTIVITY

This invention relates to novel salts of 1,3-bis-(β-ethylhexyl)-5-amino-5-methyl-hexahydropyrimidine, processes for producing these salts and their use especially in compositions having bacteriostatic activity.

1,3-Bis-(β-ethylhexyl)-5-amino-5-methyl-hexahydropyrimidine which is also known under the general designation "hexetidine" (formula I) is used above all as antiseptic for the oral mucous membrane due to its antimicrobial activity.

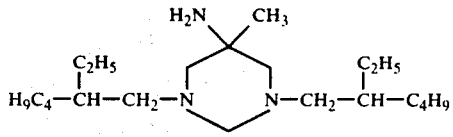

In the synthesis of hexetidine according to M. Seukus J. Am. Chem. Soc., 68 (1946) 1611-1613 which is currently usual in practice, by-products constituting 20 to 30% of the synthesis crude product are formed. The separation of these by-products by fractional distillation meets with difficulties in practice because the boiling ranges of hexetidine and of the by-products chiefly formed are very similar. These by-products include above all $N_1,N_3$-bis-(β-ethylhexyl)-2-methylpropane-triamine-(1,2,3), i.e. the "triamine", and 2,6-bis-(β-ethylhexyl)-hexahydro-7-α-methyl-1H-imidazo[1,5-c]imidazole, i.e. "hexedine." The by-products present in the raw hexetidine cause substantial undesirable side effects. For example, they have a considerable detrimental effect on the taste when using hexetidine or its salts as antiseptics of the mouth and pharyngeal cavities.

The proposal to produce pure hexetidine by a different synthesis route has not been accepted in practice. Instead of this process, a plurality of processes for purifying the above-mentioned raw hexetidine through sparingly soluble salts were proposed. For example, the following acids forming a sparingly soluble salt with the raw hexetidine were claimed: naphthalene-1,5-disulfonic acid (German Pat. No. 2,011,078), nicotinic acid (German Offenlegungsschrift No. 2,310,337 and German Pat. No. 2,310,338) and oxalic acid (German Offenlegungsschrift No. 2,323,150).

According to these prior art teachings, the reactions are carried out in most cases in the presence of heat and part of them with the use of a large excess of acid. The resultant salt must be recovered from the solution either by precipitation with water or by concentration of the solvent under vacuum, and recrystallization for further purification may be necessary.

It is an object of this invention to convert raw hexetidine, especially a commercial grade raw hexetidine of the type mentioned above, in a simple manner into an absolutely pure product which may then be used as active ingredient in bacteriostatic compositions. To this end, the invention uses novel salts of hexetidine which are formed when reacting the raw hexetidine with specific aromatic carboxylic acids and are characterized by being sparingly soluble in ordinary organic solvents at room temperature so that they are obtained in a salt-forming reaction within a solvent as pure precipitated products and may then be used as such as the active agent in compositions having bacteriostatic activity or for the recovery of pure hexetidine.

In a first embodiment, the invention is directed to novel salts of 1,3-bis-(β-ethylhexyl)-5-amino-5-methyl-hexahydropyrimidine (hexetidine) of the general formula I with aromatic carboxylic acids of the general formula II

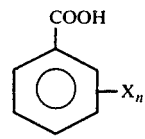

wherein n is a member out of 1 and 2 and in cases where n = 1 the substituent X is a member selected from the group consisting of —COOH, —OH, —NH$_2$, —SO$_3$H and —SO$_2$NH with the proviso that X as —COOH or —OH stands in 4-position and that in cases where n = 2, X has the previous meaning with the proviso that the X groups are different.

It has been found surprisingly that hexetidine forms sparingly soluble salts with carboxylic acids of the general formula II or reactive carboxylic acid derivatives such as their salts at room temperature in ordinary organic solvents while the by-products usually present in technical raw hexetidine form readily soluble salts with the same acids so that it is possible in this manner without great expense to separate the technical starting base into hexetidine or hexetidine salt and the undesirable by-products.

Accordingly, the invention permits the direct preparation of hexetidine products of high purity with low requirements of power, solvents and acid while simultaneously obtaining high yields. The novel salts are further distinguished by stability in storage and inertness with respect to taste and, therefore, offer important advantages in the field of using them in compositions having bacteriostatic activity.

In a first embodiment of the invention, particular importance is to be attributed to hexetidine salts which have been produced with carboxylic acids of the general formula II wherein only one substituent X is present at the aromatic group. While in cases where X is —COOH and —OH the substitution in 4-position is mandatory, the position of these substituents in 4-position, i.e. in p-position with respect to the carboxyl group, may be particularly preferred also for the other meanings of X mentioned above.

Within this class of acids of the general formula II, particular importance is to be attributed to two members, i.e. terephthalic acid (X = —COOH in 4-position) and 4-sulfamoylbenzoic acid.

Terephthalic acid has been found to be particularly useful for the effective separation of hexetidine from its accompanying by-products, especially the triamine and hexedine. Terephthalic acid is precipitated from raw hexetidine solutions in suitable solvents at room temperature in a high yield as a salt which contains 2 moles of hexetidine per mole of terephthalic acid. The salt which is obtained in very pure state can be separated mechanically from the soluble constituents of the reaction mixture with only little final washing. It may then be used as such as active ingredient having bacteriostatic characteristics but may especially also be used as intermediate product for preparing pure hexetidine from its raw mixtures. The pure hexetidine base is liberated from this salt and also from a different salt according to the invention in a manner known per se, e.g. by adding the salt to an alkaline aqueous solution and extraction with an organic solvent which is immiscible with water such as petroleum ether, methylene chloride or benzene. The pure hexetidine is then obtained by careful distillation of the solvent under vacuum.

At room temperature which is preferably used, the other acids of the general formula II generally form salts with hexetidine in a molar ratio of 1:1. These salts may also be used effectively for separating pure hexetidine from its by-products produced in the commercial synthesis. Particular importance in this respect is to be attributed to the corresponding salt of hexetidine with 4-sulfamoyl-benzoic acid. This salt is characterized by being comparatively readily soluble in aqueous alcoholic systems and simultaneously by high stability to the action of light and heat. Aqueous alcoholic solutions are stable at temperatures to as low as $-15°$ C. In addition, the pure salt is absolutely neutral with respect to the taste. Therefore, it is of particular importance within the scope of the invention for use as bactericidal active ingredient in compositions for the treatment of the mouth and laryngeal cavities.

In accordance with the invention, carboxylic acids of the general formula II having two X substituents preferably contain at least one hydroxyl group as substituent. In general this hydroxyl group is substituted in 2-position. In this embodiment, the preferred further X substituent is a $NH_2$— or a $SO_3H$ group which stands especially in 4- or 5-position.

Accordingly, the following compounds are particularly important representatives of the novel salts of hexetidine:

1,3-bis($\beta$-ethylhexyl)-5-amino-5-methyl-hexahydropyrimidineterephthalate of the formula

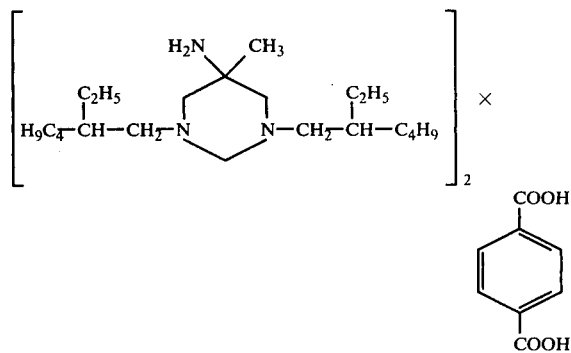

1,3-bis-($\beta$-ethylhexyl)-5-amino-5-methyl-hexahydropyrimidine-4-sulfamoyl-benzoate,
1,3-bis-($\beta$-ethylhexyl)-5-amino-5-methyl-hexahydropyrimidine-4-hydroxybenzoate,
1,3-bis-($\beta$-ethylhexyl)-5-amino-5-methyl-hexahydropyrimidine-2-aminobenzoate,
1,3-bis-($\beta$-ethylhexyl)-5-amino-5-methyl-hexahydropyrimidine-4-amino-benzoate,
1,3-bis-($\beta$-ethylhexyl)-5-amino-5-methyl-hexahydropyrimidine-4-amino-salicylate, and
1,3-bis-($\beta$-ethylhexyl)-5-amino-5-methyl-hexahydropyrimidine-5-sulfo-salicylate.

In a further embodiment, the invention is directed to a process for producing the novel salts described above of the 1,3-bis-($\beta$-ethylhexyl)-5-amino-5-methyl-hexahydropyrimidine of the formula I with the aromatic carboxylic acids having the general formula II shown above. This process is characterized in that the base is reacted with the acid in a solvent and the salt is recovered by crystallization.

The base and the acid are generally used in a molar ratio of about 1:1. However, in case of terephthalic acid and sulfobenzoic acid, 2 moles of the base are used per mole of the acid. When using raw hexetidine as the base starting material, the by-products present as contaminations are included in the stoichiometrical calculation.

The reaction can be simply carried out by mixing a solution of raw hexetidine in an organic solvent with a solution or suspension of the acid or the corresponding derivative of the acid in the molar ratio previously mentioned and allowing the mixture to stand at room temperature, if necessary or desired with stirring, until the hexetidine salt produced has been precipitated. The resultant precipitated salt is separated, washed, crystallized if desired and dried.

Suitable solvents for this reaction include especially alcohols which are liquid at room temperature, above all those containing 1 to 6 carbon atoms; aliphatic, cyclic or aromatic hydrocarbons which are liquid at room temperature; carboxylic acid esters, acid amides, ketones, aliphatic and cyclic ethers and/or nitriles. Both straight chain and branched chain alcohols may be used. A particularly suitable solvent is isopropanol. Examples of further suitable solvents include methanol, ethanol and n-propanol or butanol; ketones such as acetone or methyl ethyl ketone; ethyl or butyl acetates; low boiling point petroleum ether fractions or readily volatile hydrocarbons such as n-hexane, benzene, toluene, dimethyl formamide, ethers such as diisopropyl ether, dioxane or acetonitrile.

The salt formation in accordance with the invention may also take place in a salt exchange reaction. Thus, soluble salts of one or both reactants may be used in a manner known per se provided that disturbing precipitation side reactions do not occur in the salt exchange reaction. It may be particularly advantageous in this embodiment to use salts such as alkaline metal salts of the carboxylic acids of the general formula II.

According to a further embodiment of the invention, the novel salts of hexetidine are used as active ingredients in bacteriostatic compositions, these compositions including both cosmetic preparations and pharmaceutical compositions. In these preparations and compositions, the active ingredient according to the invention is present as usual in mixture with diluents and/or carriers. If necessary or desired, other antimicrobial agents and compositions may also be used in the peparations and compositions.

In this embodiment, the invention is especially directed to palliativa and purifying compositions inhibiting the growth of microorganisms in the region of the mouth cavity in the form of any preparation which is suitable for this purpose. Examples hereof include gargarisms, gargles, mouth lotions, mouthwashing concentrates, mouth sprays, sucking troches or tablets, toothpaste in conventional form or transparent toothpaste, chewing gum, gingiva ointments, cremes or gels.

The salts of the present invention when incorporated into compositions of this kind exhibit high antimicrobial activity against gram-positive cocci, gram-negative germs and certain fungi. Therefore, the physiologically acceptable compositions are very active for preventing bacterial infections, especially by organisms which are normally found in the mouth cavity. They may be administered orally or topically.

The bactericidal active ingredient of the present invention may consist of one or more of the salts described above and may also be used in mixture with conventional antimicrobial agents. In general, the quantity of active ingredient or combination of active ingredients in the composition is 0.01 to 2% per dose unit. Known pharmaceutically acceptable solvents and/or carrier materials and/or solvent intermediaries and/or emulsifiers are used for the routes of administration mentioned above. Examples hereof include ethanol, glycerol and other pharmaceutically acceptable alcohols and/or water-miscible solvents for gargarisms, gargles, mouth lotions and mouthwashing concentrates; cane sugar or sweetening agents such as saccharin together with one or more inert materials as binding agents, fillers or lubricants for sucking troches and tablets; insoluble phosphates as polishing agents such as dicalcium phosphate and suitable fluorine-containing compounds such as sodium monofluorophosphate as anti-caries agent for toothpastes. The salts of the present invention may also be incorporated in commercially available chewing gum bases. Sugar-free carrier mixtures may be preferred.

The salts of the present invention were subjected to bacteriological assays by the serial dilution method in a liquid nutrient medium. In these tests, the growth of the test organisms is determined with decreasing concentrations of the active ingredient in a liquid nutrient medium. After the incubation, the final concentration of the substance which still has an inhibitory effect is recorded as what is known as the MIC (minimal inhibitory concentration). For details, reference is made to E. Brunner, G. Macheck "Die Antibiotika," Verlag Hans Carl, Nuernberg, 1962, and P. Klein "Bakteriologische Grundlagen der chemotherapeutischen Laboratoriumspraxis," Springer-Verlag, Berlin-Goettingen-Heidelberg 1957.

A standard I nutrient bouillon (E. Merck, Darmstadt) which contained 2% of added glucose was used as the nutrient medium. The MIC and the minimal bactericidal concentration (MBC) were determined for five microorganisms, viz. for

*Staphylococcus aureus (Staph. aureus)*
*Proteus sp.*
*Pseudomonas aeruginosa (Ps. aerug.)*
*Streptococcus faecalis (Str. faecalis)*
*Candida albicans (Cand. alb.)*

The starting solution used was a solution having a concentration of 100 mg. base (based on the particular hexetidine salt used) per 100 ml of solvent.

In the results obtained, the MIC against the gram-positive test organisms (*Str. faecalis* and *Staph. aureus*) ranges between 1.25 and 2.5 µl./ml. nutrient medium as compared with about 500 µl./ml. nutrient medium against the gram-negative bacteria (*Proteus sp.* and *Ps. aerug.*) For the yeast *Cand. alb.*, the MIC was higher in most cases by about a power of ten as compared with the gram-positive bacteria.

The MBC for the gram-positive bacterial test organisms was also very low and about one dilution stage above the MIC. The situation is similar in case of *Cand. alb.* The MBC for the gram-negative microorganisms was 500 µl./ml. of nutrient medium.

The toxicity was determined by means of the method of Litchfield and Wilcoxon (J. Pharmacol. exp. Therap., 96 (1949) 99). The $DL_{50}$ values determined by this method for mice ranged between 1,200 and 2,500 mg./kg. p.o.

This invention will now be illustrated by, but is not necessarily limited to, the following examples.

EXAMPLE 1

17.0 Grams of raw hexetidine (about 80%) are dissolved in 15 ml. isopropanol. To the solution is added with stirring a suspension of 4.2 g. of terephthalic acid in 35 ml. isopropanol. After stirring for about 3 hours, the reaction mixture is allowed to stand overnight at room temperature. The color turns to pink. The precipitate is separated and washed with little ether or acetone and dried. Melting point, 155°–156° C.

Yield: 15.1 g. = 89% of the theory based on "hexetidine" contained in the starting mixture.
$C_{50}H_{96}N_6O_4$: molecular weight 845.37

|  | C | H | N |
|---|---|---|---|
| Calculated: | 71.04% | 11.45% | 9.94% |
| Found: | 70.64% | 11.50% | 9.95% |

EXAMPLE 2

6.8 Grams of raw hexetidine (about 80%) and 4.0 g. of 4-sulfamoyl-benzoic acid are dissolved in about 40 ml. of isopropanol at room temperature while stirring. After a short reaction time, a white precipitate separates. The precipitate is recovered after some time by suction filtration, washed with little isopropanol and dried.

Melting point, 134°–135° C.
Yield: 6.6 g. = 76% of the theory based on "hexetidine" contained in the starting amount.
$C_{28}H_{52}N_4O_4S$: Molecular weight: 540.82

|  | C | H | N |
|---|---|---|---|
| Calculated: | 62.18% | 9.69% | 10.36% |
| Found: | 62.05% | 9.73% | 10.28% |

EXAMPLE 3

6.8 Grams of raw hexetidine (= about 80% of hexetidine) and 2.7 g. of 4-amino-benzoic acid are reacted in 30 ml. isopropanol as described in Example 2. The product is washed with little ether and dried.
Melting point: 118°–120° C.

EXAMPLE 4

10.2 Grams of raw hexetidine (= about 80% of hexetidine) are dissolved in 20 ml. of isopropanol. To the solution is added a solution of 4.2 g. of 4-hydroxybenzoic acid in 40 ml. of isopropanol while stirring. After a short reaction time, a white precipitate separates. The reaction mixture is processed as described in Example 2.
Melting point: 155°–156° C.

EXAMPLE 5

6.8 Grams of raw hexetidine (= about 80% of hexetidine) and 3.0 g. of 4-amino-2-hydroxy-benzoic acid are dissolved in 40 ml. isopropanol while stirring. After a short period of time, a precipitate is separated. The reaction mixture is processed as described in Example 3.
Melting point: 141°–143° C.

EXAMPLE 6

3.4 Grams of raw hexetidine (= about 80%) and 1.4 g. of 2-amino-benzoic acid are dissolved in 20 ml. of isopropanol while stirring at room temperature. After stirring for 8 hours, the mixture is allowed to stand overnight in a refrigerator. The product is recovered by suction filtration, washed with a small amount of isopropanol and dried.
Melting point: 98°–100° C.

EXAMPLE 7

6.8 Grams of raw hexetidine (= about 80% of hexetidine) and 2.5 g. of 2-hydroxybenzoic-5-sulfonic acid (+ 2 moles water of crystallization) are reacted in 40 ml. of isopropanol by the procedure of Example 6. The acid salt is produced.
Melting point: 153°–156° C.

EXAMPLE 8

17.0 Grams of raw hexetidine (= about 80% of hexetidine) are added to 50 ml. of methanol and heated to 50° C. Than 4.2 g. of terephthalic acid are added in portions. The mixture is stirred for additional 30 minutes and then about half of the solvent is distilled off under vacuum at about 40° C. The mixture is allowed to cool, and the precipitated compound is recovered on a suction filter, washed with little ether and dried.

Yield: 11.8 g. = about 68% based on hexetidine in the amount charged.
Melting point: 154°–155° C.

EXAMPLE 9

17.0 Grams of raw hexetidine (= about 80%) and 10.0 g. of 4-sulfamoyl-benzoic acid are dissolved in 100 ml. of ethanol at room temperature while stirring. After stirring for about 5 hours, the mixture is allowed to stand overnight in a refrigerator. After concentration under vacuum to about half the volume, a white precipitate separates while the mixture is cold. The precipitate is recovered on a suction filter and washed with about 25 ml. of ether/methanol (95:5).
Melting point: 134°–136° C.

EXAMPLE 10

17.0 Grams of raw hexetidine (= about 80%) and 10.0 g. of 4-sulfamoyl-benzoic acid are dissolved in 100 ml. of n-propanol at room temperature while shaking. After shaking for 6 hours, the solution is allowed to stand overnight in a refrigerator. After scratching with a pointed glass rod, a precipitate separated suddenly. The product was recovered on a suction filter and washed with about 30 ml. of ether.
Melting point: 133°–136° C.

EXAMPLE 11

The procedure of Example 10 was repeated except that 100 ml. of acetone were substituted for n-propanol.
Melting point: 134°–135° C.

EXAMPLE 12

6.8 Grams of crude hexetidine (about 80% hexetidine) are dissolved in 40 ml. n-butanol. To the solution are added in portions 3.9 g. of 4-sulfamoylbenzoic acid while stirring at room temperature. After stirring for 6 hours, the solution is allowed to stand overnight in a refrigerator. The precipitate formed is recovered on a suction filter and washed with little ether.
Melting point: 134°–135° C.

EXAMPLE 13

6.8 Grams of crude hexetidine (about 80%) are dissolved in 40 ml. of petroleum ether (40°–60° C.). 4.0 Grams of 4-sulfamoylbenzoic acid are added in small portions while stirring. After stirring for about 2 hours, the mixture has accepted the form of a grayish translucent gel. The product is recovered on a suction filter and recrystallized from about 25 ml. of isopropanol.
Melting point: 134°–135° C.

EXAMPLE 14

The procedure of Example 13 was repeated except that 50 ml. n-hexane were substituted for 40 ml. petroleum ether. The residue was washed with about 20 ml. of ether/methanol (95:5).
Melting point: 133°–135° C.

EXAMPLE 15

17.0 Grams of crude hexetidine (about 80%) are dissolved in 100 ml. benzene while shaking. Then 10.0 g. of 4-sulfamoylbenzoic acid are added in portions while shaking at room temperature. After shaking for 8 hours, the mixture is allowed to stand overnight in a refrigerator. The crystal slurry is recovered on a suction filter and washed with about 30 ml. of ether/methanol (95:5).
Melting point: 134°–136° C.

EXAMPLE 16

The procedure of Example 15 is repeated except that 100 ml. ethyl acetate are substituted for the benzene.
Melting point: 134°–135° C.

EXAMPLE 17

17 Grams of crude hexetidine (about 80%) and 10.0 g. of 4-sulfamoylbenzoic acid are dissolved in 75 ml. of dimethyl formamide. After stirring for 5 hours at room temperature, the solution is allowed to stand overnight in a refrigerator. The solution is then concentrated under vacuum to half of its volume. Ether is added thereby precipitating the salt which is recrystallized from about 40 ml. of isopropanol and washed with about 20 ml. of ether.
Melting point: 133°–135° C.

EXAMPLE 18

6.8 Grams of raw hexetidine (about 80% of pure hexetidine) and 2.6 g. of monosodium-4-sulfobenzoate × 2H$_2$O are stirred in 40 ml. of ethanol at room temperature. After stirring for 8 hours, the mixture is allowed to stand overnight at room temperature whereupon the solution is separated from undissolved matter. The precipitate obtained after concentration under vacuum is recovered on a suction filter and washed first with 40 ml. of acetone and then with a small amount of ether.

Melting point: 152° C.
Di-hexetidine-4-sulfobenzoate:

$C_{49}H_{96}N_6O_5S$: molecular weight, 881.42

|  | C | H | N |
|---|---|---|---|
| Calculated: | 66.77% | 10.98% | 9.53% |
| Found: | 66.37% | 11.02% | 9.50% |

EXAMPLE 19

6.8 Grams of crude hexetidine (about 80% of pure hexetidine) and 4.0 g. of 4-sulfamoyl-benzoic acid are stirred in 40 ml. of diisopropyl ether for 4 hours at room temperature. After standing overnight, the mixture is subjected to suction filtration. The precipitate is thoroughly washed three times with diisopropyl ether and dried.

Melting point: 128°–131° C. After recrystallization from isopropanol, the salt has a melting point of 134°–136° C.

EXAMPLE 20

6.8 Grams of crude hexetidine (about 80% pure hexetidine) are dissolved in 15 ml. of cyclohexane at room temperature while stirring. To the solution is added a suspension of 4.0 g. of 4-sulfamoylbenzoic acid in 25 ml. of cyclohexane while stirring. After stirring for 6 hours at room temperature, the mixture is allowed to stand overnight in a refrigerator. The precipitate is recovered by suction filtration and washed with little ether.

Melting point: 126°–129° C. After recrystallization from isopropanol: 134°–136° C.

EXAMPLE 21

The procedure of Example 18 is repeated except that 40 ml. of tetraline are substituted for the cyclohexane.
Melting point: 133°–135° C.

EXAMPLE 22

17.0 Grams of crude hexetidine (about 80%) are dissolved in 100 ml. of butyl acetate at room temperature. To the solution are added 10.0 g. of 4-sulfamoylbenzoic acid in portions at room temperature while shaking. After shaking for 8 hours at room temperature, the mixture is allowed to stand overnight in a refrigerator. The crystal slurry is recovered on a suction filter and washed with little ether.
Melting point: 134°–135° C.

EXAMPLE 23

6.8 Grams of crude hexetidine (about 80%) are dissolved in 40 ml. of acetonitrile at room temperature while stirring. To the solution are added 4.0 g. of 4-sulfamoylbenzoic acid in portions while stirring. Stirring is continued for further 5 hours at room temperature. The mixture is then allowed to stand overnight in a refrigerator. The crystalline precipitate is recovered on a suction filter and washed with little ether.
Melting point: 134°–135° C.

EXAMPLE 24

6.8 Grams of crude hexetidine (about 80% pure hexetidine) and 4.0 g. of 4-sulfamoylbenzoic acid are dissolved in 40 ml. of dioxane at room temperature while stirring. Stirring is continued for further 5 hours whereupon the solution is allowed to stand overnight in a refrigerator. The precipitate separated from the mixture is recovered, washed with a small amount of ether and recrystallized from isopropanol.
Melting point: 135°–136° C.

EXAMPLE 25

6.8 Grams of crude hexetidine (about 80%) and 4.0 g. of 4-sulfamoylbenzoic acid are dissolved in 40 ml. of methyl ethyl ketone at room temperature while stirring. Stirring is continued for further 5 hours whereupon the solution is allowed to stand overnight in a refrigerator. The crystalline precipitate separated from the mixture is recovered, washed with a small amount of ether and dried.
Melting point: 134°–136° C.

EXAMPLE 26

To recover pure hexetidine from its crude product, 84.5 g. of 1,3-bis-($\beta$-ethylhexyl)-5-amino-5-methyl-hexahydropyrimidine terephthalate obtained by the process described in Example 1 are added to 3,000 ml. of 1N NaOH. Then 500 ml. of petroleum ether (b.p. 60°–80° C.) are added and the mixture is stirred until the salt is completely dissolved. The organic phase is separated, washed with water and dried over sodium sulfate. The solvent is then distilled off under vacuum. The yield of pure hexetidine is 61 g. (about 90% of the theory).

Recipes for various compositions containing the novel hexetidine salts of the present invention and having bacteriostatic activity are illustrated in the following examples. In the particularly preferred embodiment, these compositions contain the salt of hexetidine with 4-sulfamoylbenzoic acid.

EXAMPLE 27

Solution: 1 table-spoon amount undiluted for mouth-washing or gargling

| "Hexetidine" salt | 0.1 to 0.4 g. |
|---|---|
| Ethanol 96% | 10.0 to 25.0 g. |
| Nonionic emulsifier | 0.5 to 2.0 g. |
| Aromatic oil | 0.2 to 0.5 g. |
| Water | ad 100.0 g. |

EXAMPLE 28

Mouth-wash concentrate, mouth lotion: As mouth-wash 1 tea spoon in ½ glass of water; as mouth lotion: 20 to 40 drops in ½ glass of water.

| "Hexetidine" salt | 1.0 to 4.0 g. |
|---|---|
| Ethanol 96% | 30.0 to 50.0 g. |
| Nonionic emulsifier | 4.0 to 8.0 g. |
| Saccharin sodium | 0.1 to 0.4 g. |
| Aromatic oil | 6.0 to 8.0 g. |
| Water | ad 100.0 g. |

EXAMPLE 29

Chewing gum: 100 strips of 1.0 g. each are prepared from the batch.

| Chewing gum base | 15.0 to 18.0 g. |
|---|---|
| Glucose syrup 43° Be | 20.0 to 25.0 g. |
| Powdered sugar | 55.0 to 65.0 g. |
| "Hexetidine" salt | 1.0 to 4.0 g. |
| Glycerol | 0.2 to 0.5 g. |
| Aromatic oil | 0.2 to 0.5 g. |
| Water | ad 100.0 g. |

EXAMPLE 30

Sucking tablet: 200 tablets of 0.5 g. each are prepared from 100 g.

| | |
|---|---|
| "Hexetidine" salt | 2.0 to 8.0 g. |
| Saccharin sodium | 0.3 to 0.7 g. |
| Menthol | 0.4 to 0.8 g. |
| Mixture of mono- and diglycerides of higher fatty acids | 10.0 to 40.0 g. |
| Sorbitol granules | ad 100.00g. |

EXAMPLE 31

Toothpaste:

| | |
|---|---|
| Carboxymethylcellulose | 0.5 to 2.0 g. |
| Armorphous silicic acid | 2.0 to 4.0 g. |
| Glycerol DAB 7 | 15.0 to 30.0 g. |
| "Hexetidine" salt | 0.1 to 0.4 g. |
| 4-Hydroxybenzoic acid ester | 0.05 to 0.2 g. |
| Saccharin sodium | 0.1 to 0.3 g. |
| Sodium monofluorophosphate | 0.6 to 1.0 g. |
| Dicalcium phosphate dihydrate | 25.0 to 30.0 g. |
| Dicalcium phosphate anhydride | 0.8 to 2.0 g. |
| Sodium lauryl sulfate | 1.5 to 3.0 g. |
| Aromatic oil | 1.0 to 2.0 g. |
| Water | ad 100.0 g. |

EXAMPLE 32

Transparent toothpaste:

| | |
|---|---|
| Carboxymethylcellulose | 0.25 to 1.5 g. |
| 4-Hydroxybenzoic acid ester | 0.05 to 0.2 g. |
| Polyethylene glycol 400 | 3.0 to 5.0 g. |
| Glycerol 1.26 g./ml. | 50.0 to 75.0 g. |
| "Hexetidine" salt | 0.1 to 0.4 g. |
| Sodium monofluorophosphate | 0.6 to 0.9 g |
| Saccharin sodium | 0.1 to 0.3 g. |
| High purity precipitated silicic acid | 17.0 to 22.0 g. |
| Sodium lauryl sulfate | 1.0 to 2.0 g. |
| Aromatic oil | 0.75 to 1.5 g. |
| Water | ad 100.0 g. |

The disclosure herein other than the use of the salts for inhibiting growth of microorganisms in the region of the mouth cavity is attributable to just two of us, namely, Dr. Kunz and Dr. Posselt. Salts disclosed herein and the process of purifying hexetidine utilizing salts disclosed herein are disclosed and claimed in application Ser. No. 738,210, filed Nov. 3, 1976.

What is claimed is:

1. The method of treating the mouth cavity for inhibiting the growth of microorganisms therein which comprises applying thereto an effective amount of a composition containing at least one salt of 1,3-bis-(β-ethylhexyl)-5-amino-5-methyl-hexahydropyrimidine of the general formula

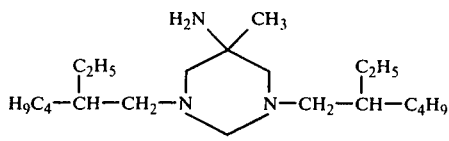

with an aromatic carboxylic acid of the general formula

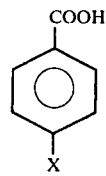

wherein X is a member selected from the group consisting of —COOH, —OH, —NH₂, —SO₃H and —SO₂NH₂, as active ingredient together with at least one member selected from the group consisting of conventional diluents and carrier materials.

2. Method of treating the mouth cavity according to claim 1 characterized, that compositions are used which contain 1,3-bis-(β-ethylhexyl)-5-amino-5-methylhexahydropyrimidine-terephthalate of the formula

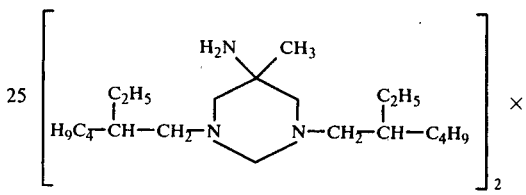

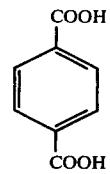

3. Method of treating the mouth cavity according to claim 1 characterized, that compositions are used which contain 1,3-bis-(β-ethylhexyl)-5-amino-5-methylhexahydropyrimidine-4-sulfamoyl-benzoate.

4. Method of treating the mouth cavity according to claim 1 characterized, that compositions are used which contain 1,3-bis-(β-ethylhexyl)-5-amino-5-methylhexahydropyrimidine-4-hydroxybenzoate.

5. Method of treating the mouth cavity according to claim 1 characterized, that compositions are used which contain 1,3-bis-(β-ethylhexyl)-5-amino-5-methyl-hexahydropyrimidine-4-amino-benzoate.

6. Method of treating the mouth cavity according to claim 1 characterized, that compositions are used which contain 1,3-bis-(β-ethylhexyl)-5-amino-5-methyl-hexahydropyrimidine-4-sulfo-benzoate.

7. Compositions having bacteriostatic activity, suitable for inhibiting growth of microorganisms in the region of the mouth cavity, said compositions containing at least one salt of 1,3-bis-(β-ethylhexyl)-5-amino-5-methyl-hexahydro-pyrimidine of the general formula

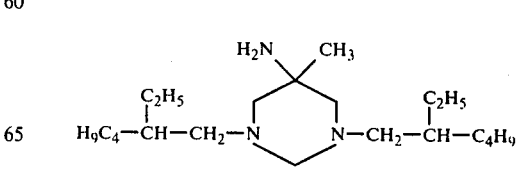

with an aromatic carboxylic acid of the formula

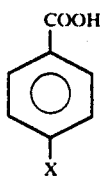

wherein X is a member selected from the group consisting of —COOH, —OH, —NH$_2$, —SO$_3$H and —SO$_2$NH$_2$, as active ingredient together with at least one member selected from the group consisting of conventional diluents and carrier materials.

8. Composition of claim 7, wherein X is —COOH.
9. Composition of claim 7, wherein X is —SO$_2$NH$_2$.
10. Composition of claim 7, wherein X is —OH.
11. Composition of claim 7, wherein X is —NH$_2$.
12. Composition of claim 7, wherein X is —SO$_3$H.

* * * * *